(12) United States Patent
Cho et al.

(10) Patent No.: US 10,036,073 B2
(45) Date of Patent: Jul. 31, 2018

(54) SLIDE CHIP FOR DETECTION SENSOR OF FOOD-BORNE PATHOGENS AND PREPARATION METHOD THEREOF

(75) Inventors: Young Jin Cho, Seoul (KR); Chul Jin Kim, Gyeonggi-do (KR); Nam Soo Kim, Seoul (KR); Chong Tai Kim, Gyeonggi-do (KR); Jin Soo Maeng, Gyeongsangnam-do (KR); Tae Eun Kim, Gyeonggi-do (KR); Myung Hyun Lee, Seoul (KR)

(73) Assignee: KOREA FOOD RESEARCH INSTITUTE, Gyeonggi-do (KR)

( * ) Notice: Subject to any disclaimer, the term of this patent is extended or adjusted under 35 U.S.C. 154(b) by 108 days.

(21) Appl. No.: 14/343,213

(22) PCT Filed: Feb. 22, 2012

(86) PCT No.: PCT/KR2012/001336
§ 371 (c)(1),
(2), (4) Date: Mar. 6, 2014

(87) PCT Pub. No.: WO2013/018969
PCT Pub. Date: Feb. 7, 2013

(65) Prior Publication Data
US 2014/0287424 A1 Sep. 25, 2014

(30) Foreign Application Priority Data

Aug. 4, 2011 (KR) .......................... 10-2011-0077756

(51) Int. Cl.
| | |
|---|---|
| C12Q 1/68 | (2018.01) |
| C12Q 1/689 | (2018.01) |
| C12Q 1/04 | (2006.01) |
| G01N 33/543 | (2006.01) |
| G01N 33/553 | (2006.01) |
| G01N 33/569 | (2006.01) |
| G01N 33/50 | (2006.01) |
| C12N 15/11 | (2006.01) |

(52) U.S. Cl.
CPC ............... *C12Q 1/689* (2013.01); *C12Q 1/04* (2013.01); *G01N 33/5017* (2013.01); *G01N 33/54366* (2013.01); *G01N 33/553* (2013.01); *G01N 33/56911* (2013.01); *G01N 33/56916* (2013.01); *G01N 33/56938* (2013.01); *C12N 15/111* (2013.01); *C12N 2310/16* (2013.01); *C12N 2320/10* (2013.01)

(58) Field of Classification Search
None
See application file for complete search history.

(56) References Cited

U.S. PATENT DOCUMENTS

2006/0014172 A1* 1/2006 Muller ..................... B82Y 5/00
435/6.11

OTHER PUBLICATIONS

Hwang, J. et al., Nucleic Acids Symposium Series, No. 44, pp. 253-254 (2000).*
Kim, Y. S. et al., Analytica Chimica Acta, vol. 634 (2), pp. 250-254 (Dec. 25, 2008).*
Tombelli, S. et al., Biomolecular Engineering, vol. 24 (2), pp. 191-200 (Jun. 2007).*

* cited by examiner

*Primary Examiner* — J. Hines
*Assistant Examiner* — Khatol Shahnan Shah
(74) *Attorney, Agent, or Firm* — Vorys, Sater, Seymour and Pease LLP; Mih Suhn Koh

(57) ABSTRACT

The present invention relates to a slide chip for a sensor for detection of food-borne bacteria and a fabrication method thereof. More particularly, the invention relates to a slide chip for a sensor for detection of food-borne bacteria and a fabrication method thereof, the slide chip comprising: a substrate coated with a metal; a linker having a substituent which may be bonded to the metal and is located at the 5' end of deoxythymidine (dT); and a food-borne bacterium-derived RNA aptamer that is bound to the linker by the 3'-end poly A tail. The slide chip makes it possible to detect food-borne bacteria in a rapid and accurate manner.

5 Claims, 6 Drawing Sheets

SLIDE CHIP FOR DETECTION SENSOR OF FOOD-BORNE PATHOGENS AND PREPARATION METHOD THEREOF

TECHNICAL FIELD

The present invention relates to a slide chip for a sensor for detection of food-borne bacteria, which is based on an aptamer that binds specifically to food-borne bacteria, and to a fabrication method thereof.

BACKGROUND ART

Food poisoning refers to illness caused by eating foods contaminated with chemical or natural toxins. With respect to food poisoning incidents in Korea, the number of food poisoning patients increased by 17 times for 16 years from 618 patients in the year 1990 to 10,833 patients in the year 2006, and the ratio of patients per food poisoning incident also increased by about 2.16 times (41 persons in the year 2006). In addition, with an increase in food service and the development of the food service industry, the scale of food poisoning incidents has increased and the number of food poisoning incidents also has continuously increased. For this reason, the uneasy feeling of people to foods has increased, and ensuring the safety of foods by preventing or minimizing hazards resulting from foods in order to keep healthy living is of increasing importance.

Food poisoning is illness caused by chemical or natural toxins and is mostly caused by food-borne pathogenic bacteria. Thus, efforts to detect pathogenic bacteria in foods have been made, and methods for detecting pathogenic bacteria in foods include traditional analysis methods employing biochemical properties, and molecular biological methods that have recently been developed. The traditional analysis methods are labor-intensive and time-consuming, and for this reason, molecular biological methods for detecting pathogenic bacteria in foods have recently received attention.

With methods for detection of pathogenic bacteria, which have been studied based on molecular biology, developed immunological methods of measuring antigens specific to bacterial strains using antibodies include immunochromatography, immunoliposomes, etc. In addition, genetic methods generally include amplifying a specific DNA sequence of a bacterial strain by PCR and analyzing the amplified sequence, and genes to be analyzed by such genetic methods include toxin genes in pathogenic bacterial strains, protein genes that are expressed in pathogenic bacteria, repetitive DNA sequences that are intermittently dispersed on the genome of prokartotic cells, 16S rRNA genes, etc. In addition, Kim et al. developed a non-labeled immunosensor capable of detecting *Pseudomonas aeruginosa* (that causes deterioration) and attempted to apply a biosensor for detection of pathogenic bacteria.

However, the developed detection method as described above has not yet been actively commercialized, and there has been a continued demand for the accuracy of detection results and a decrease in detection costs. Accordingly, there is an urgent need for the development of a system and method of detecting food-borne bacteria in a rapid and accurate manner.

DISCLOSURE

Technical Problem

It is an object of the present invention to provide a slide chip for a sensor for detection of food-borne bacteria, which can detect food-borne bacteria in a rapid and accurate manner by the use of an aptamer that binds specifically to food-borne bacteria, and a fabrication method thereof.

Technical Solution

The present invention provides a slide chip for a sensor for detection of food-borne bacteria, the slide chip comprising: a substrate coated with a metal; a linker having a substituent which is capable of being bound to the metal and is located at the 5' end of deoxythymidine (dT); and a food-borne bacterium-derived RNA aptamer that is bound to the linker by polyadenylic acid located at the 3' end. The present invention also provides a method for fabricating the slide chip.

The present invention also provides a method for fabricating a slide chip for a sensor for detection of food-borne bacteria, the method comprising the steps of: spin-coating silver ion solution on a substrate to a thickness of 25-35 nm to form a silver nano-film; binding a linker, which has a thiol group located at the 5' end of deoxythymidine (dT), to an RNA aptamer against an antigenic lipopolysaccharide molecule that is the cell wall polymer of *E. coli* O157:H7, an RNA aptamer that binds to ompC protein of a *Salmonella typhimurium* strain, or an RNA aptamer against teichoic acid of *Staphylococcus aureus*, thereby preparing an RNA aptamer-linker complex; and binding the thiol group of the RNA aptamer-linker complex to the silver coated on the substrate, thereby immobilizing the RNA aptamer-linker complex onto the silver nano-film.

Advantageous Effects

The use of the inventive slide chip for a sensor for detection of food-borne bacteria makes it possible to detect food-borne bacteria in a rapid and accurate manner. Particularly, the slide chip of the present invention is useful for detection of living bacteria.

The inventive slide chip for a sensor for detection of food-borne bacteria is fabricated in a simple manner.

MODE FOR INVENTION

The present invention is directed to a slide chip for a sensor for detection of food-borne bacteria, which can detect food-borne bacteria in a rapid and accurate manner, and to a fabrication method thereof. The slide chip according to the present invention comprises: a substrate coated with a metal; a linker having a substituent which is capable of being bound to the metal and is located at the 5' end of deoxythymidine (dT); and a food-borne bacterium-derived RNA aptamer bound to the linker by the 3'-end poly A tail.

Hereinafter, a slide chip according to the present invention, a fabrication method thereof and a method of detecting food-borne bacteria using the slide chip will be described in further detail by way of example.

While the following description will be made on the basis of an *E. coli* O157:H7 strain, it will be apparent to those skilled in the art that an RNA aptamer that binds to ompC protein of a *Salmonella typhimurium* strain, and an RNA aptamer for teichoic acid of *Staphylococcus aureus*, which are described in Korean Patent Application Nos. 10-2010-0129763 and 10-2010-0129767, respectively, filed on Dec. 17, 2010, may be used in the following examples.

(A) Preparation of Aptamer (1) Aptamer

Figure 1:
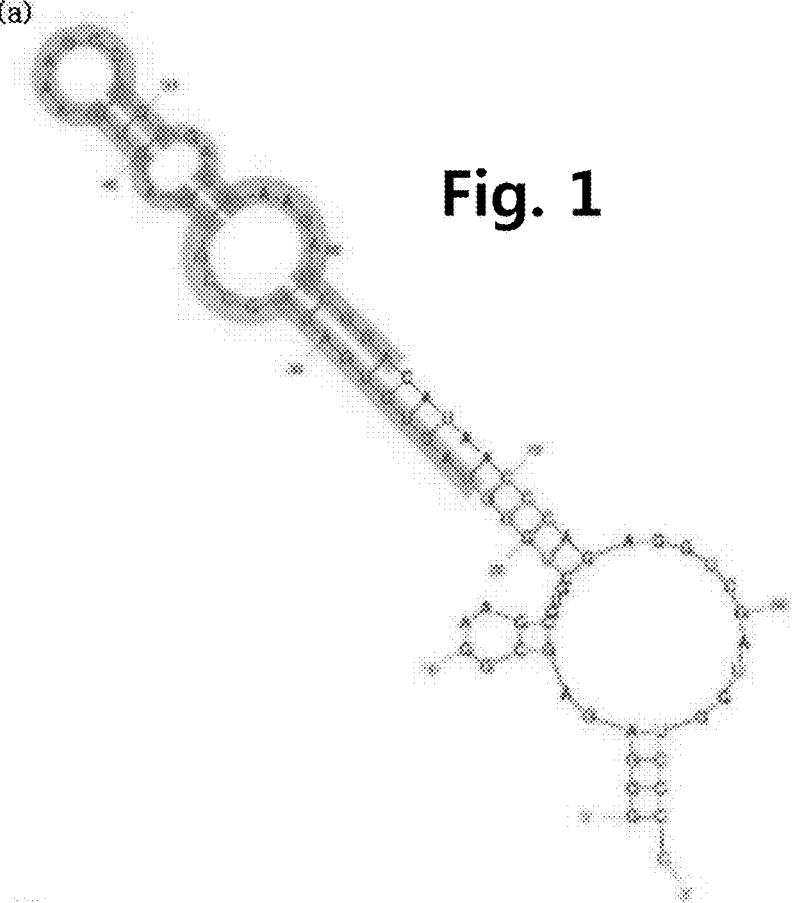
FIG. 1 shows the secondary structure of an RNA aptamer of the present invention and the fluorination of pyrimidine (cytosine and uracil).
Figure 1:
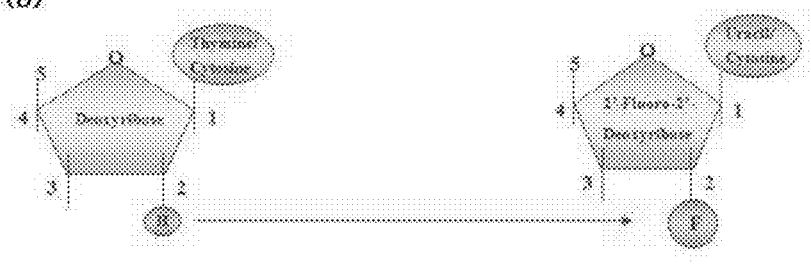

An RNA aptamer was prepared using, as an antigen, a lipopolysaccharide (LPS) molecule that is the cell wall polymer of the food-borne bacterium *E. coli* O157:H7. As shown in FIG. 1, in this aptamer, fluorine (F) was attached to the 2' carbon of RNA pyrimidine (C/U) to impart resistance to RNase to thereby increase the stability of the RNA molecule. To bind a dT-ligand molecule to the aptamer molecule, a 16-mer poly (A) tail was added to the 3' end.

Figure 2:
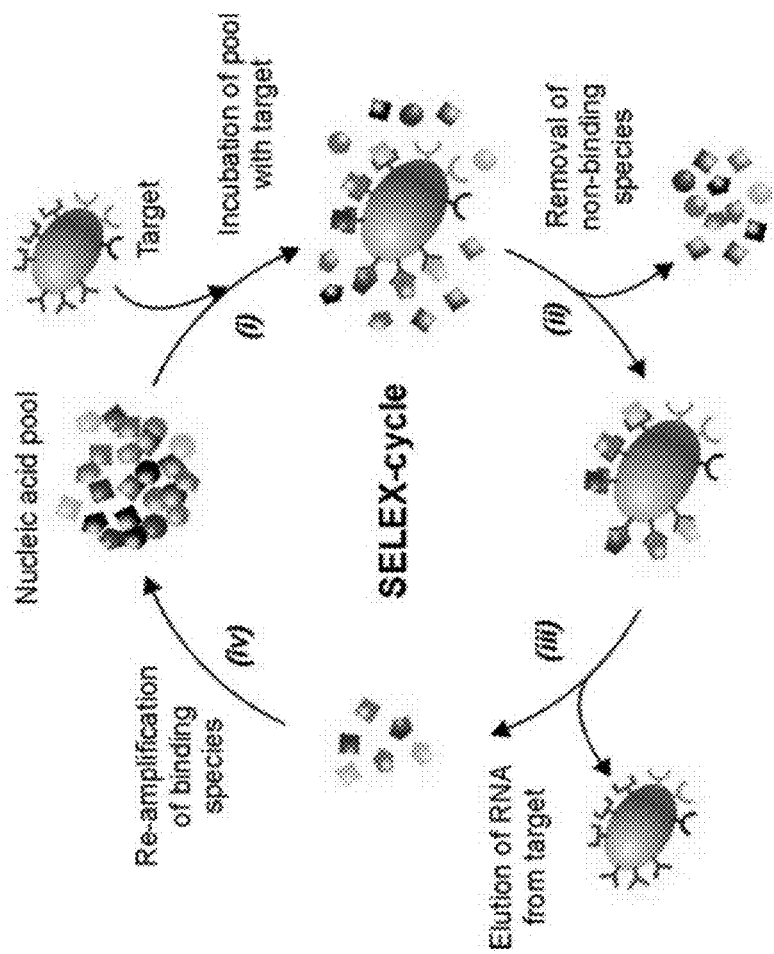
FIG. 2 is a schematic view of a SELEX process cycle, which shows (i) binding, (☐) removal of non-bound molecules, (☐) selection of a complex, and (☐) amplification of the selected complex.

This aptamer was built by an in vitro process called systematic evolution of ligands by exponential enrichment (SELEX) of FIG. 2 for a lipopolysaccharide (LPS) molecule that is the cell wall polymer of *E. coli* O157:H7.

In addition, methods for preparing an RNA aptamer ompC protein of a *Salmonella typhimurium* strain and an RNA aptamer against teichoic acid of *Staphylococcus aureus* are similar to the method for preparation of the aptamer against *E. coli* O157:H7.

(2) Linker

Figure 3:
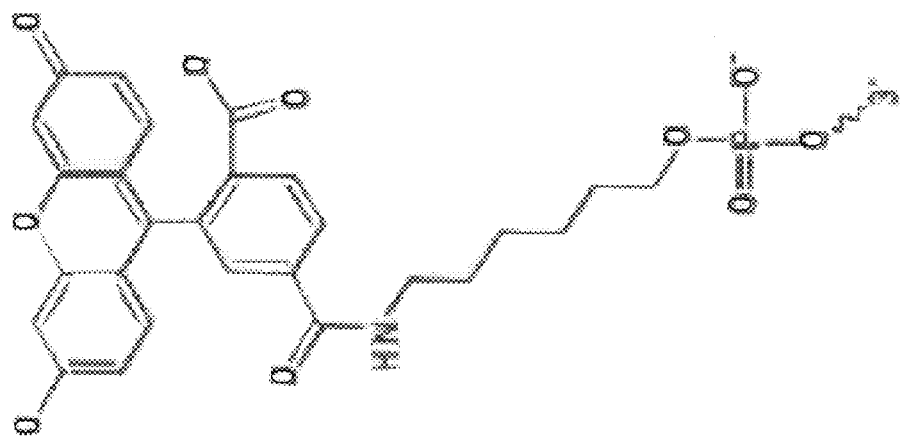
FIG. 3 shows the structure of a 6-FAM molecule.
Figure 4:
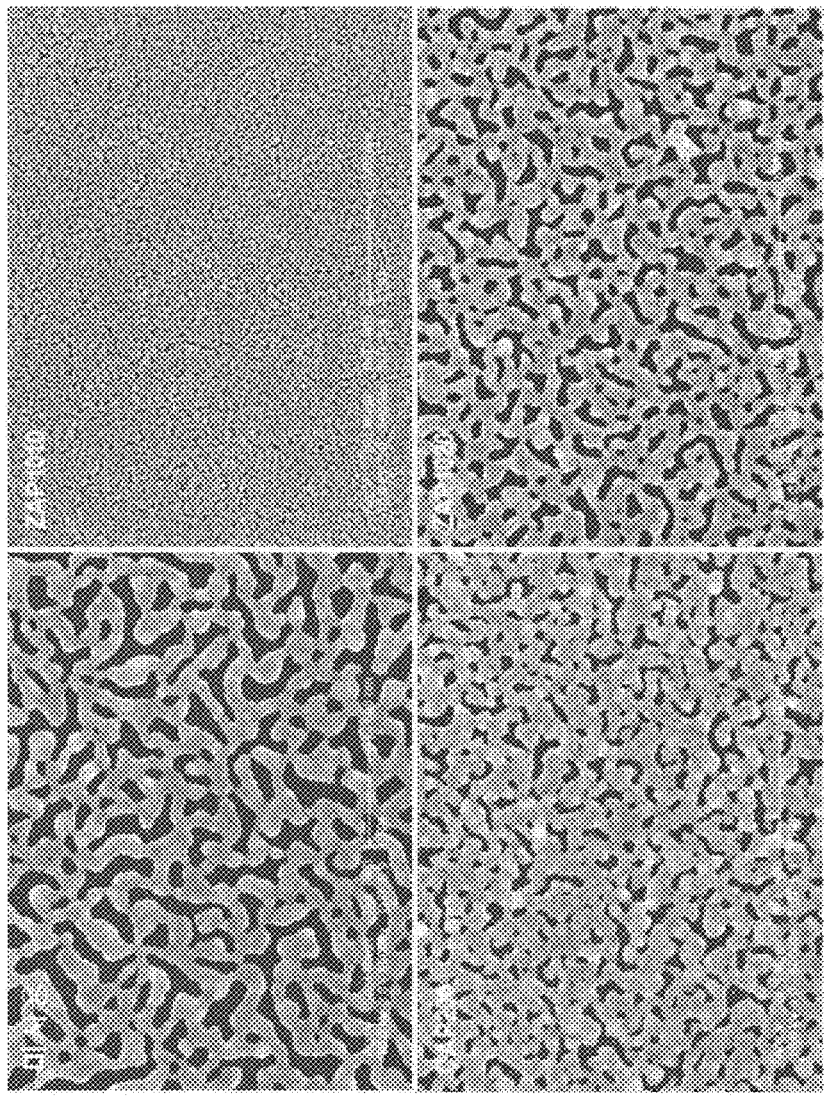
FIG. 4 shows a silver nano-film.

As a linker that is used to immobilize the above-described aptamer or attach a tag, the following dT-ligand was used.

dT-SH: a ligand (linker) molecule that is used to immobilize the aptamer onto the silver or gold surface and consists of 16 mer-deoxythymidine (16-dT) for hybridization with the 3' end poly(A) tail of the aptamer.

dT-FAM: a linker molecule having a fluorescent 6-FAM molecule at the 5' end of 16-dT for hybridization with the 3' end poly(A) tail of the aptamer. FAM in FIG. 3 is a fluorescence tag having fluorescence properties with excitation peak at 495 nm and emission peak of 520 nm.

(B) Construction of Aptamer-Based System on Silver Nano-Film

The aptamer-based system was constructed on a silver nano-film spin-coated with silver ion solution to a thickness of 25-35 nm, which is a transparent biolinker slide that can be easily observed by an optical microscope or a fluorescence microscope.

(1) Preparation of Silver Nano-Film

Preparation of substrate: glass (BK7) was washed with isopropyl alcohol (IPA), acetone and distilled water and dried.

Spin coating of surface adhesion co-catalyst amino-trimethoxy silane: amino-trimethoxy silane was spin-coated at 3000 rpm for 30 seconds, and then cured on a hot plate at 110° C. for 2 minutes.

A silver nano-film was prepared while controlling the thickness of the film according to the degree of silver ion solution with IPA and the spin coating speed.

The resulting film was cured on a hot plate at a temperature of 130~150° C. for 3 minutes, thereby completing the silver nano-film.

(2) Hybridization (Annealing Reaction) of RNA Aptamer with dT-Ligand

A) Mixing:

(a) In order to allow all dT-SH on the nano-film to bind to the aptamer molecule, the molar ratio of the RNA aptamer to dT-SH was adjusted to 2:1, and the RNA aptamer and dT-SH were used at concentrations of 20 µM and 10 µM. To activate the thiol group, 10% 0.1M DTT solution was added to the mixture.

(b) For hybridization with a dT-FAM linker for making a fluorescence-labeled aptamer, in order to label the RNA aptamer with a fluorescence tag, the RNA aptamer and dT-FAM were used at a molar ratio of 1:2 and at concentrations of 20 µM and 40 µM, respectively.

Buffer used to dilute the RNA aptamer and dT-FAM to the above-described concentrations was 50 mM sodium phosphate buffer (pH 7.4).

B) Hybridization: the reaction mixture was heated at 65° C. for 5 minutes, and then cooled at room temperature for 10 minutes.

(3) Immobilization of RNA Aptamer onto Silver Nano-Film

In this experiment, direct immobilization by a thiol group was used, and the aptamer was used at a concentration of 10 µM.

Washing: washing of the silver nano-film was performed in the following manner: reaction with 1.2 N NaOH solution for 5 minutes, washing three times with distilled water, reaction with 1.2 N HCl solution for 5 minutes, reaction with concentrated HCl for 1 minute, washing three times with distilled water, and then drying.

Activation: 10% 0.1 M DTT solution in 50 mM sodium-phosphate buffer (pH 7.4) was added during the hybridization process in order to activate the thiol group (—SH) that can bind to silver by a reduction reaction of —SH required for immobilization of the aptamer.

Immobilization: To immobilize the aptamer onto the silver nano-film, 0.5 µL of the aptamer-dT-SH mixture was spotted on the nano-film and reacted at room temperature for 30 minutes. Then, the film washed three times with distilled water, and then washed with 50 mM sodium phosphate buffer (pH 7.4).

(4) Treatment of Immobilized Aptamer with Bacterial Sample

Preparation of bacteria: Food-borne *E. coli* O157:H7 cells were shake-cultured in nutrient broth medium at 37° C. for 12 hours. The culture was harvested by centrifugation at 3500×g for 10 minutes and suspended with the same volume of PBS (pH 7.0) to remove impurities other than bacterial cells. The concentration of bacterial cells in the bacterial cell-PBS suspension was adjusted to $1 \times 10^8$ cells by measurement of the absorbance at a wavelength of 600 nm, thereby preparing a bacterial sample.

Treatment with bacterial sample: The suspension of *E. coli* O157:H7 bacteria in PBS was spotted onto O157-immobilized silver nano-film and incubated at room temperature for 30 minutes to induce binding, and then unbound cells were removed by washing with PBS (pH 7.0).

(C) Microscopic Observation of Aptamer-Biolinker System Immobilized on Silver Nano-Film In order to microscopically observe food-borne bacteria bound specifically to each aptamer and to confirm the bound bacteria by fluorescence, treatment of a fluorescence-labeled aptamer was performed, followed by observation with a fluorescence microscope.

(1) Observation with Optical Microscope

The sample prepared as described above was observed with an optical microscope (Eclipse 50i, Nikon) having ×40 (Plan Fluor/0,75, DIC) and ×60 (Plan Fluor/0,85, WD) objective lenses, and the microscopic image was processed with Visilog 6 (Noesis) software.

(2) Observation with Fluorescence Microscope

Treatment of fluorescence-labeled aptamer: 20 μM of the above-prepared fluorescence-labeled aptamer solution composed of the O157 aptamer bound to dT-FAM (excitation wavelength=495 nm, and emission wavelength=520 nm) was dropped onto each spot and incubated at room temperature for 1 hour to induce binding, and unbound cells were removed by washing with PBS (pH 7.0).

Observation of fluorescence-labeled aptamer: The above-described sample was observed with a fluorescence microscope (Eclipse 80i, Nikon) having a B2-A filter (Ex; 450-490, DM; 505, BA; 520) and ×40 and ×60 objective lenses (Plan Fluor), and the bacterial cells bound to each aptamer were analyzed by an image caused by fluorescence from the fluorescence-labeled aptamer.

(D) Results

Figure 5:
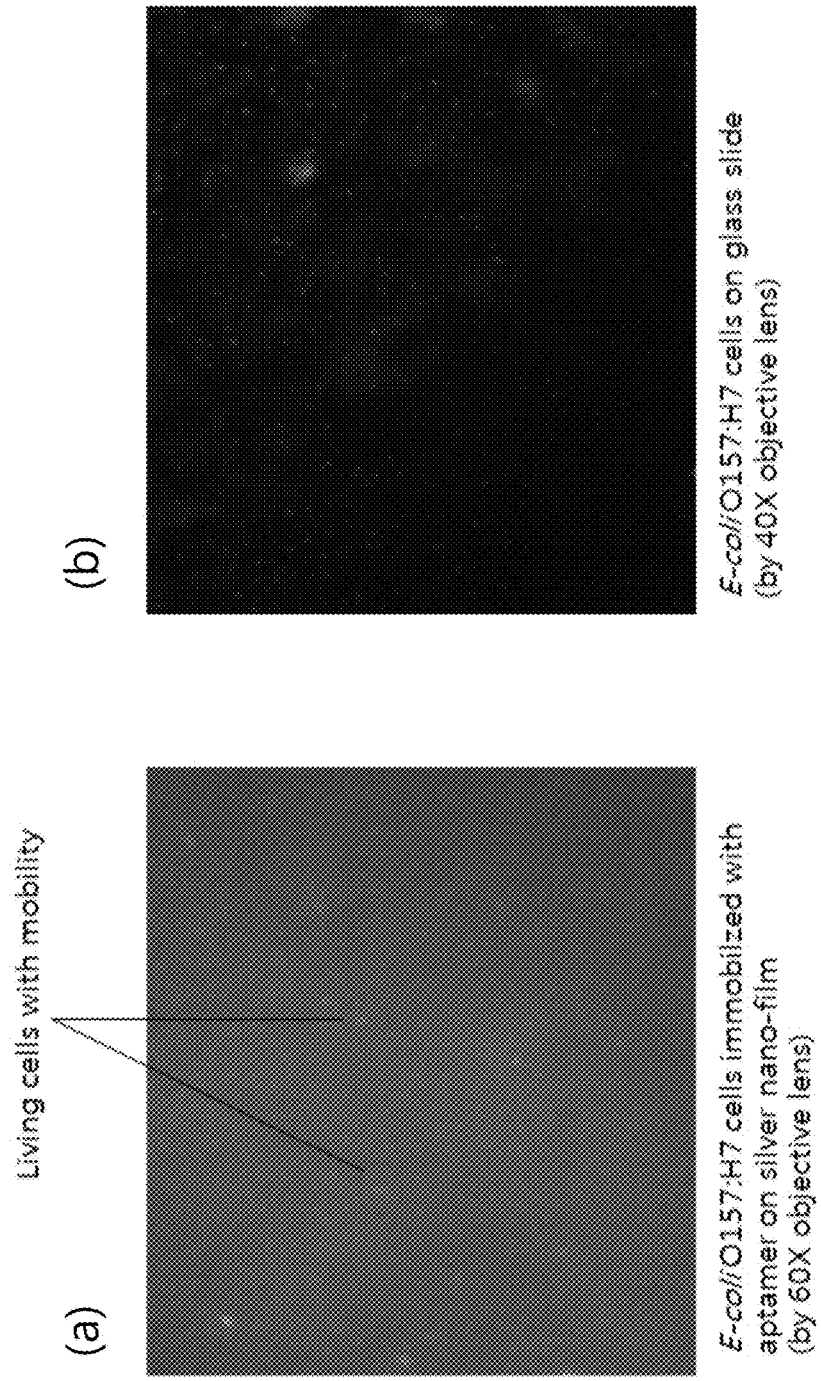
FIG. 5 shows the results obtained by forming a silver nano-film on a slide glass for an optical microscope, binding an O157 aptamer to the surface of the nano-film, and then trapping O157 bacteria.
Figure 6:
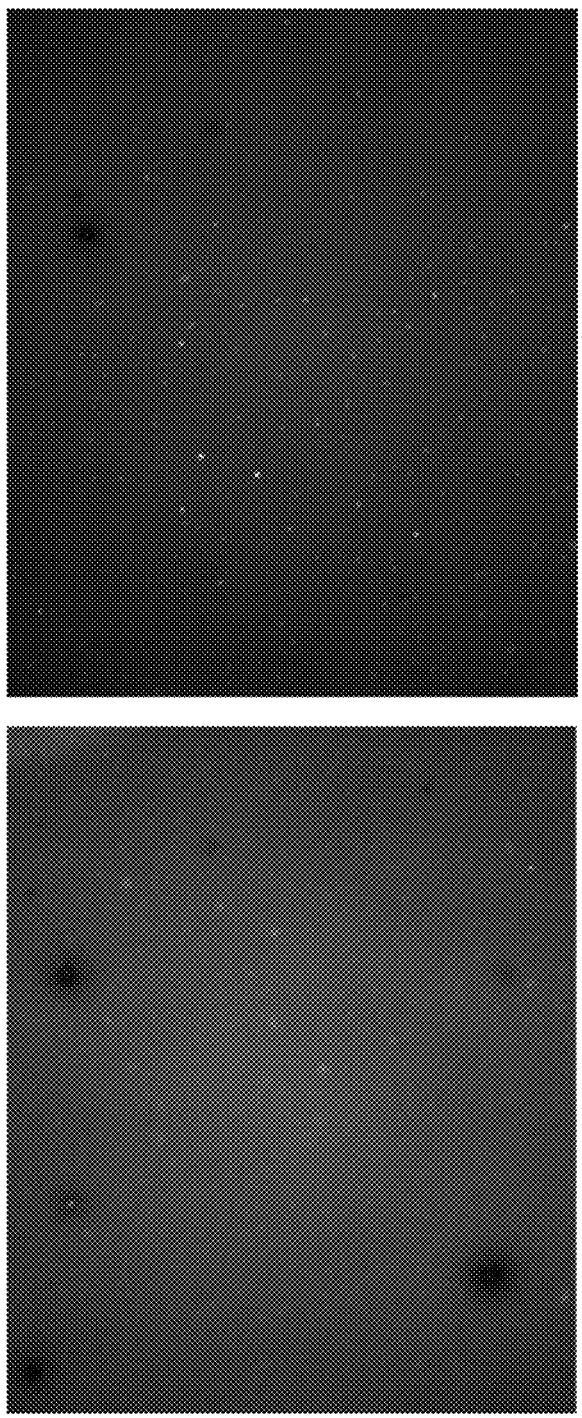
FIG. 6 shows the results obtained by effectively observing living O157 bacteria by a chip designed such that a thiol-conjugated O157 aptamer traps living O157 bacteria and a fluorescent aptamer expresses the presence of the bacteria.

FIGS. 5 and 6 show the results obtained by selectively trapping only O157 bacterial cells with the O157 aptamer. Specifically, FIG. 5 show the results obtained by immobilizing living bacterial cells without labeling and observing the cells with an optical microscope, and FIG. 6 shows the results obtained by observing bacterial cells with a fluorescence microscope using a fluorescence tag attached to the aptamer.

FIG. 5(a) shows the results obtained by forming a silver nano-film on slide glass for an optical microscope, linking the O157 aptamer to the surface of the nano-film, and then trapping O157 bacterial cells with the aptamer. As shown in the figure, only O157 bacterial cells could be trapped by washing PBS, and thus mobile living cells could be accurately observed. FIG. 5(b) shows the results obtained by dropping the O157 bacterial cell solution onto slide glass and observing the bacterial cells, and as shown in FIG. 5(b), the presence of living bacterial cells could be visually observed, but the presence of other foreign matter made it difficult to accurately observe living bacterial cells.

As shown in FIG. 6, the thiol group-conjugated O157 aptamer trapped living O157 bacterial cells, and living O157 bacterial cells could be effectively observed by the chip designed such that the fluorescent aptamer expresses the presence of the bacterial cells. FIG. 6(a) shows the results obtained by observing cultured O157 cells without washing, and FIG. 6(b) shows the results obtained by trapping living bacterial cells washed with PBS, and there was little or no difference between the two cases.

In addition, the presence of other pathogenic bacteria, including *Salmonella typhimurium* and *Staphylococcus aureus*, could be detected, similar to the presence of the O157 strain. The use of the slide chip for detection of food-borne bacteria, fabricated by the above-described method, made it possible to detect even only one food-borne bacterium.

The invention claimed is:

1. A slide glass for an optical microscope for detection of food-borne bacteria comprising:
   a glass substrate nano-coated with a metal;
   a linker having a substituent bonded to the metal and located at the 5' end of deoxythymidine (dT); and
   an RNA aptamer bonded to the linker by the 3'-end poly A tail,
   wherein the RNA aptamer is an aptamer binding to lipopolysaccharide of *E. coli* O157:H7, an aptamer binding to ompC protein of *Salmonella typhimurium* strain, or an aptamer binding to teichoic acid of *Staphylococcus aureus*.

2. The slide glass of claim 1, wherein the RNA aptamer is obtained by substituting the 2' carbon of RNA pyrimidine (cytosine and uracil) with fluorine.

3. The slide glass of claim 1, wherein the metal is silver or gold.

4. The slide glass of claim 1, wherein the substituent is a thiol group (—SH).

5. The slide chip of claim 1, wherein the slide glass further comprises a fluorescence tag having a 6-FAM molecule for fluorescence labeling of food-borne bacteria bonded to the RNA aptamer, the fluorescence tag is being located at the 5' end of deoxythymidine (dT).

* * * * *

UNITED STATES PATENT AND TRADEMARK OFFICE
CERTIFICATE OF CORRECTION

| | |
|---|---|
| PATENT NO. | : 10,036,073 B2 |
| APPLICATION NO. | : 14/343213 |
| DATED | : July 31, 2018 |
| INVENTOR(S) | : Yong Jin Cho et al. |

It is certified that error appears in the above-identified patent and that said Letters Patent is hereby corrected as shown below:

On the Title Page

Item (75)
Delete "Young Jin Cho" and replace with -- Yong Jin Cho --

Signed and Sealed this
Fourth Day of August, 2020

Andrei Iancu
*Director of the United States Patent and Trademark Office*